United States Patent [19]

Xia et al.

[11] Patent Number: 5,648,505

[45] Date of Patent: Jul. 15, 1997

[54] METHOD FOR THE PREPARATION OF A NOVEL C-RING PRECURSOR FOR TAXOIDS AND NOVEL INTERMEDIATES

[76] Inventors: Zhi-Qiang Xia, NE. 535 Maiden La. 211, Pullman, Wash. 99163; Esko Karvinen, Järvitie 4 E 43, FIN-90550 Oulu; Ari Koskinen, Lepikkotie 2 A 1, FIN-90460 Oulunsalo, both of Finland

[21] Appl. No.: 447,843

[22] Filed: May 23, 1995

Related U.S. Application Data

[63] Continuation-in-part of Ser. No. 266,561, Jun. 28, 1994, abandoned.

[51] Int. Cl.$^6$ .................................................. C07D 317/72
[52] U.S. Cl. ........................................... 549/333; 549/336
[58] Field of Search ....................................... 549/333, 336

[56] References Cited

PUBLICATIONS

Holton et al., J. Am. Chem. Soc., 1994, No. 116, pp. 1597–1598, "First Total Synthesis of Taxol. 1. Functionalization of B Ring."

Holton et al., J. Am. Chem. Soc., 1994, No. 116, pp. 1599–1600, "First Total Synthesis of Taxol. 2. Completion of the C and D Rings."

Nicolaou et al., Letters to Nature, vol. 367, 17 Feb. 1994, pp. 630–634, "Total synthesis of taxol."

Hajos et al., Organic Synthesis, 63, 26 (1985), pp. 26–36, "(+)-(7aS)-2,3,7,7a-Tetrahydro-7a-Methyl-1H-Indene-1, 5-(6H)-Dione ... "

Nitz et al., Tetrahedron Letters, vol. 25, No. 29, 1984, pp. 3047–3050, "Chemoselective Ethylene Acetalization of α,β-Unsaturated vis-a-vis ... "

Hudson et al., Synlett, Nov. 1992, pp. 867–868, "Acetal Formation During the Catalytic Hydrogenation of Cyclic α,β-Unsaturated Ketones."

Philip S. Bailey, J. Am. Chem. Soc., 1956, No. 78, pp. 3811–3816, "The Oxonolysis of Phenanthrene in Methanol."

Di Giovanni et al., Tetrahedron, vol. 49, No. 48, pp. 11321–11328, 1993, "A Stereoselective Synthesis of 3(R)–Hydroxy–2(s)–ornithine."

Mancuso et al., J. Org. Chem., vol. 43, No. 12, 1978, pp. 2480–2482, "Oxidation of Long–Chain and Related Alcohols to Carbonyls by Dimethyl Sulfoxide ... ".

Brown, RF et al CA 102: 184987 (1984).

Brown, RF et al CA 98: 179252 (1983).

*Primary Examiner*—Amelia Owens
*Attorney, Agent, or Firm*—Adduci, Mastriani & Schaumberg, L.L.P.

[57] ABSTRACT

The present invention relates to a process for the preparation of a compound of the formula (VIII) or (IX) useful as precursor for the C-ring in taxanes

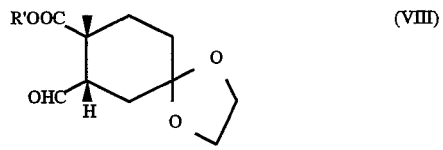

(VIII)

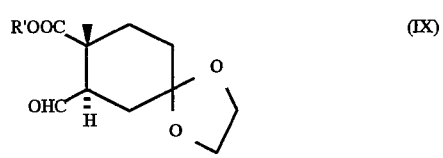

(IX)

wherein R' is a $C_1$–$C_6$-alkyl. The invention further relates to the novel compounds (VIII) and (IX) and to novel intermediates in said process.

14 Claims, No Drawings

METHOD FOR THE PREPARATION OF A NOVEL C-RING PRECURSOR FOR TAXOIDS AND NOVEL INTERMEDIATES

This application is a continuation-in-part of 08/266,561 filed Jun. 28, 1994 now abandoned.

FIELD OF THE INVENTION

The present invention provides a method for the preparation of a novel C-ring precursor for the ring system of taxoids. The invention provides further novel intermediates useful in said method.

BACKGROUND OF THE INVENTION

The publications and other materials used herein to illuminate the background of the invention, and in particular, cases to provide additional details respecting the practice, are incorporated by reference.

Taxoids or taxanes are highly complex diterpenes many of which exhibit promising antineoplastic activity. The anti-cancer active compound taxol is the most frequently cited taxane derivative in the literature. This compound was several decades ago isolated from the bark of the Pacific Yew (*Taxus brevifolia*) (Wani M C et al., J Am Chem Soc 1971, 93, 2325). Taxol has shown high activity against many tumor cell line systems. It has shown excellent activity, particularly in the treatment of advanced ovarian cancer, either as such or in combination with other anti-cancer drugs. It has also been successful in the treatment of breast cancer, lung cancer, melanoma and several other cancers, too. (For clinical usage of taxol, see Rowinsky E et al., J Natl Cancer Inst 1990; 82:1247–1259).

The taxol molecule (1) is shown in Scheme 1. The molecule comprises a side chain attached no a complex ring system built up of the A-, B-, C and D-rings. Synthetic approaches to taxol and its derivatives have been extensively described in the literature (see for example Boa, Jenkins and Lawrence, Contemporary Organic Synthesis, 1994, 1, 47; Nicolaou K C et al., Angew Chem Int Ed Engl 1994, 33, 15). Despite extensive attempts, no successful total synthesis of taxol has been published until very recently (Nicolaou K C et al., Nature 1994, 367, 630; Holton R A et al., J Am Chem Soc 1994, 116, 1597; Holton R A et al., ibid, 1994, 116, 1599). To avoid the problem of direct extraction of taxol from the bark of yew trees, semisynthetic methods for the production of taxol have also been developed. The compound 10-deacetylbaccatin III (compound 2 in Scheme 2), which constitutes the ring system of taxol, can be derived from renewable needles and twigs of the yew tree. The introduction of the side chain into the 13-position of 10-deacetylbaccatin yields taxol or derivatives thereof.

The advent of chemotherapy based on taxol and its derivatives has, however, been hampered by shortcomings relating to their limited availability. Another disadvantage, particularly relating to taxol, is the low aqueous solubility. As a result of the low water solubility, formulations have been made that based on surfactants giving rise to adverse effects in some patients. Thus, there is a great need to develop a synthesis that could be used for the large scale production of taxol as well as for the production of more water soluble taxane derivatives.

Both of the problems concerning the limited availability of taxol as well as its low water solubility can be solved through the development of a sufficiently flexible entry into taxol and its structural analogues. The inventors of the present invention have recently initiated a program with this as a major goal (Koskinen A M P et al., J Chem Soc Chem Commun, 1994, 21).

Scheme 2 discloses the structure of the some taxanes with anti-cancer activity as well as 10-deacetylbaccatin III and baccatin III, compounds useful as starting materials in the semi-synthesis of taxol or its analogues. The structure of the side chain is responsible for the water solubility of the molecule. Compounds 5 to 8 (Scheme 2) have proved to have higher solubility in water than taxol itself. (See Nicolaou K C et al., Angew Chem Int Ed Engl 1994, 33, 15).

SUMMARY OF THE INVENTION

The present invention relates to a process for the preparation of a compound of the formula (VIII) or (IX) useful as precursor for the C-ring in taxanes

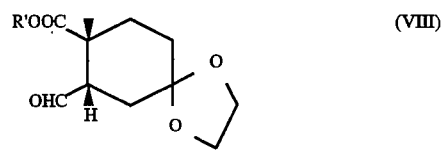

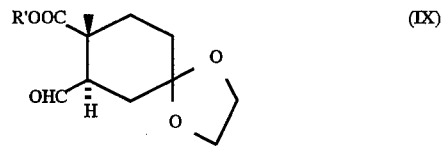

wherein R' is a $C_1$–$C_6$-alkyl. The process comprises the steps of a) ketal protecting of the carbonyl group and isomerizing of the double bond in a compound of the formula (I) for formulae see Scheme 3), to give a compound of the formula (II)

b) treating the compound (II) with diazabicyclooundecane (DBU) in a suitable solvent, preferably a lower alcohol of 1 to 5 carbon atoms or acetonitrile, to give a compound of the formula (III)

c) either i) ozonolyzing the compound (III) in methanol followed by oxidative work-up with basic hydrogen peroxide, or ii) oxidizing compound (III) with ruthenium tetraoxide ($RuO_4$) generated in situ from $RuCl_3$ with e.g. sodium periodate, to give the diacid (IV)

d) either i) treating the diacid (IV) from step c) with a diazoalkane of 1 to 6 carbon atoms in diethylether in the presence of an acid, or ii) alkylating the diacid (IV) with a $C_1$–$C_6$-alkyl halide, to give the diester (V)

e) reducing the diester of formula (V) with diisobutyl-aluminiumhydride (DIBAL) in toluene to give the compound (VI)

f) opening the lactone ring of compound (VI) by treating said compound with basic lower alcohol of 1 to 5 carbon atoms followed by treatment with a diazoalkane of 1 to 6 carbon atoms to give a compound of formula (VIII, and g) subjecting the compound (VII) to Swern oxidation in the presence of oxalyl chloride [$(COCl)_2$], dimethyl-sulfoxide (DMSO) and triethylamine to give the compound of formula (VIII) and optionally epimerizing compound (VIII) in the presence of DBU to give a mixture of compound (VIII) and compound (IX) which further is separated into the compounds (VIII) and (IX) by e.g. HPLC.

The novel compounds of formulae (VIII), (IX) and (II) to (VII) are also within the scope of the invention.

DETAILED DESCRIPTION OF THE INVENTION

The novel process of this invention as well as the novel C-ring precursor obtained by said process and the novel intermediates used therein are disclosed in Scheme 3. The synthesis can be started with The R-enantiomer of the Hajos-Parrish ketone (compound I), prepared in standard fashion utilizing D-proline catalysis (Hajos Z G and Parrish D R, J Org Chem 1974, 39, 1615; Halos Z G and Parrish D R, Org Synth 1985, 63, 26). Ketal protection of the enone carbonyl function with concomitant isomerisation of the double bond to give compound II can be performed with ethylene glycol, collidinium p-toluene sulfonate in benzene according to literature conditions (Nitz T J and Paquette L A, Tetrahedron Lett., 1984, 25, 3047). It is worth noting that according to a recent report (Hudson P and Parson P J, Synlett 1992, 867) the major product observed under these conditions was the five-membered ring isomerised ketal of the formula

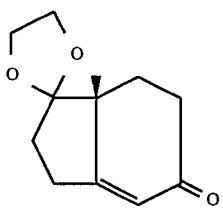

In these experiments, this compound was obtained only after prolonged exposure to the reaction conditions.

The isomerisation of the double bond in compound II into conjugation with the carbonyl functionality to give compound III is preferably performed by treating compound II with diazabicycloundecane (DBU) in ethanol. Alternatively, compound III can be prepared from compound II e.g. by refluxing in acetonitrile in the presence of DBU (Jin Z and Fuchs P L, J Am Chem Soc 1994, 116, 5995). Treatment of compound II with hydroxide bases (KOH, NaOH) (Heather J B et al., J Am Chem Soc 1976, 98, 3661) lead to mixtures of the desired compound III and 1,4-addition products with the alcohol, said 1,4-addition products having the formula

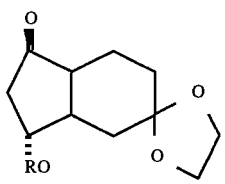

Elimination of these 1,4-addition products with a base will give compound III. The cleavage of the enone (compound III) into the one-carbon eliminated diacid (IV) can be performed by ozonolysis of compound III followed by oxidative work-up with basic hydrogen peroxide (Bailey P S, J Am Chem Soc, 1956, 78, 3811). Alternatively, compound IV can be prepared from compound III by oxidation with ruthenium tetraoxide (RuO$_4$) generated An situ from RuCl$_3$ with e.g. sodium periodate, in a mixture of carbon tetrachloride, acetonitrile and water (Webster F X et al., J Org Chem 1987, 52, 689). Treatment of the crude oxidation product (IV) with diazomethane gives the methyl ester (compound V) Alternatively, compound V can be prepared from compound IV by methylation with methyl iodide in dimethylformamide in the presence of sodium hydrogen carbonate (Bocchi V et al., Synthesis, 1979, 961). The alkyl esters can generally be obtained by treatment with a diazoalkane of the formula R"CHN$_2$ where R" is hydrogen or an alkyl of 1 to 5 carbon atoms, or by alkylation of compound IV with a $C_1$–$C_6$-alkyl halide.

The diester of formula V can be reduced with diisobutylaluminiumhydride (DIBAL) in toluene (Di Giovanni M C et al., Tetrahedron, 1993, 49, 11321) to give the lactone (compound VI). The lactone ring in compound VI can be opened with basic methanol followed by esterification with diazomethane to give the a methyl ester according formula (VII). Treatment with diazoalkanes R"CH$_2$N$_2$ where R" is hydrogen or an alkyl of 1 to 5 carbon atoms will generally result in alkyl esters of formula (VII). Swern oxidation (Manson et al., J Org Chem, 1978, 43, 2480) of compound VII with oxalyl chloride, dimethylsulfoxide (DMSO) and triethylamine gives the taxoid C-ring precursor of formula (VIII). Compound VIII can be epimerized in dichloromethane in the presence of DBU (Dauben W G and Warshawsky, J Org Chem, 1990, 55, 3075) to give a mixture of the compounds VIII and IX which can be separated by HPLC.

The invention will be illuminated by the following non-restrictive examples.

General procedures:

The solvents were dried over appropriate drying agents (Perrin, D. D.; Armarego, W. L. F. Purification of Laboratory Chemicals 3rd ed., Pergamon Press, 1988). Thin layer chromatography was performed on silica gel 60 F$_{254}$ plates from Merck. Spots were visualized under UV light (254 nm) and by spraying with a 3% vanillin ethanol solution containing 1% H$_2$SO$_4$ followed by heating with heat gun. For flash chromatography silica gel 60 (particle size 0.040–0.063 mm) from Merck was used. GC was performed on a Perkin-Elmer 8420 GC with a β-cyclodextrin column using two methods: method 1:25 min at 150° C. then heating with a ramp raze of 20° C./min to 225° C. (iso time 5 min); method 2: heating from 150° C. with a ramp rate of 6° C./min to 225° C. (iso time 10 min). NMR spectra were recorded on a Bruker AM-200 spectrometer.

EXAMPLE 1

Compound II of Scheme 3

The compound was prepared according to conditions described in Nitz T J and Paquette L A, Tetrahedron Lett. 1984, 25, 3047. A suspension of Compound I ($[\alpha]^{20}_D$=–350° (c=1.0, toluene)) of Scheme 3 (0.131 g, 0.8 mmol), collidinium p-toluene sulfonate (0.029 g, 0.1 mmol) and ethylene glycol (0.062 g, 1 mmol) in 25 mL benzene was refluxed with azeotropic removal of water for 72 h (oil bath, 110° C.). After cooling down, 30 mL of CH$_2$Cl$_2$ was added and the solution was washed with 10 mL water. The organic solution was evaporated, and the residue was chromato-graphed on silica (hexane:EtOAc 9:1) to give Compound II (0.125 g, 0.6 mmol, 75%). TLC (hexane:EtOAc) R$_f$=0.75 (SM 0.52 ), GC (method 1) retention time 19.408 min (SM 20.365). M.p. 55°–56° C. (petroleum ether).

$[\alpha]^{20}_D$=–70° (c=1.28, toluene)

$^1$H NMR (CDCl$_3$) δ5.64–5.61 (dd, 1H), 3.95–3.78 (m, 4H), 2.9–2.86 (m, 2H), 2.43–2.39 (m, 2H), 1.84–1.45 (m, 4H), 1.11 (s, 3H).

$^{13}$C NMR (CDCl$_3$) δ220.61, 145.59, 118.01, 108.91, 64.49, 64.35, 49.94, 41.57, 37.58, 30.75, 29.53, 19.07.

HRMS: found 208.1093, calcd for C$_{12}$H$_{16}$O$_3$ 208.1099.

EXAMPLE 2

Compound III of Scheme 3

5 g of Compound II of the foregoing example and 10 g of DBU (diazabicycloundecane) were dissolved in 100 mL ethanol and the solution was refluxed for 30 min. After cooling in ice the pH was adjusted to 7 with 2N HCL at 0° C. The solution was evaporated and the residue was dissolved in 300 mL $CH_2Cl_2$, washed with water (2×50 mL). The organic solvent was evaporated and the crude product purified by silica gel chromatography (hexane:EtOAc 9:1) to give Compound III (3.3 q, 66%). TLC (Hexane:EtOAc) $R_f$=0.63, GC (method 1) retention time 23.537 min.

$[\alpha]^{20}_D$=−222° (C=2.73, toluene)

$^1$H NMR ($CDCl_3$) δ7.52 (dd, J=2.3, 5.8 Hz, 1H), 6.05 (dd, J=2.1, 5.8 Hz, 1H) 3.95–3.90 (m, 4H), 2.79 (m, 1H), 2.15–1.42 (m, 6H), 1.15 (s, 3H).

$^{13}$C NMR ($CDCl_3$) δ213.93, 166.41, 131.05, 108.53, 64.13, 63.81, 47.59, 45.85, 35.17, 31.20, 29.20, 21.74.

MS m/z (rel int) 79 (30.1), 86 (100), 91 (22.5), 99 (82.4), 121 (9.5), 165 (12.8), 180 (27.2), 208 (6.7, M$^+$). HRMS: found 208.1092, calcd for $C_{12}H_{16}O_3$ 208,1099.

EXAMPLE 3

Compound IV (R=H) of Scheme 3

Compound III (0.296 g, 1.42 mmol) was dissolved in acetonitrile (2 ml) and $CCl_4$ (2 ml). Sodium periodate (1.67 g, 7.82 mmol) was added and the mixture was stirred vigorously. A sample (0.3 ml) of stock solution containing 20 mg $RuCl_3$/ml was diluted to 3 ml with water and this solution was added all at once to the reaction mixture. The mixture heated up considerably. After some time additional amounts of the solvent system was added (1+1+1,3 ml) and the mixture was stirred at room temperature over night (21 h). Water was added to the mixture to dissolve part of the crystallized salts and the mixture was extracted with DCM (3×) and dried over $Na_2SO_4$ and concentrated to give 85 mg (25%) of compound Selected spectral data for compound IV:

$^1$H NMR ($CDCl_3$): δ9.68 (2H, br s), 3.86 (4H, s), 2.70 (1H, dd, J=9.2, 5.1 Hz), 1.36 (3H, s).

$^{13}$C NMR ($CDCl_3$): δ182.2, 179.2, 107.9, 64.3, 47.6, 42.9, 33.5, 32.1, 31.0, 24.9.

MS (CI, $NH_3$) 262 (M+18), 245 (M+1), 244, 99, 86.

EXAMPLE 4

Compound V (R=methyl) of Scheme 3

2.7 g (13 mmol) of Compound III of Example 2 was dissolved in 10 mL MeOH and the solution was cooled to −78° C. Ozone was bubbled until TLC showed complete conversion of the starting material (50 min), after which tins 10% aq NaOH (15 mL) and 30% $H_2O_2$ (10 mL) was added and the reaction mixture was brought to reflux for 30 min. After cooling to rt, the pH of the solution was adjusted to 7 with HCl. The solution was evaporated and the residue was homogenized in 200 mL ether. Acetic acid (0.3 mL) was added followed by an ethereal solution of diazomethane. The solution was filtered, evaporated and purified by silica gel chromatography (hexane:EtOAc 9:1) to give Compound V (R=methyl) (1.7 g, 48%). GC (method 2) retention tame 11.189 min.

$^1$H NMR ($CDCl_3$) δ3.97–3.89 (m, 4H), 3.678 (s, 3H, 3.675 (s, 3H), 2.73 (dd, J=4.8, 9.6 Hz, 1H), 2.26–59 (m, 6H), 1.37 (s, 3H).

$^{13}$C NMR ($CDCl_3$) δ176.14, 173.42, 107.90, 64.27, 64.22, 51.69, 51.52, 47.96, 43.96, 33.70, 32.40, 31.21, 25.01.

MS m/z (rel int) (Cl, $NH_3$) 86 (40.2), 99 (48.3), 157 (22.2), 241 (48.2), 273 (100, M$^+$+1).

HRMS: found 272.1270, calcd for $C_{13}H_{20}O_6$ 272.1260.

EXAMPLE 5

Compound VI of Scheme 3

To a solution of Compound V of the foregoing example (140 mg, 0.5 mmol) in 5 mL toluene at −78° C. was added dropwise 0.5 mmol of DIBAL (diisobutyl aluminiumhydride). The reaction mixture was stirred for 30 min at the same temperature. The treatment for 30 min with 0.5 mmol DIBAL was repeated three times (total 1.5 mmol DIBAL), after which a few drops of conc HCl was added at −78° C. and the mixture was stirred for another 10 min. The cooling bath was removed and the mixture was allowed to reach rt in 20 min. 50 mL $CH_2Cl_2$ was added, the mixture was washed with water (2×5 mL), filtered and evaporated at 40° C. (bath) to give Compound VI. Silica gel column chromatography (hexane:EtOAc 8:2) gave pure Compound VI (82 mg, 75%). GC (method 2) retention time 11.457 min, mp 64°–66° C. (hexane, ether).

$^1$H NMR ($CDCl_3$) δ4.31 (dd, J=6.2, 8.9 Hz, 1H), 4.15(dd, J=5.2, 8.9 Hz, 1H), 4.11–3.89 (m, 4H), 2.53–2.32 (m, 1H), 2.19–1.49 (m, 6H), 1.26 (s, 3H).

$^{13}$C NMR ($CDCl_3$) δ180.88, 107.57, 69.54, 64.42, 64.25, 41.64, 40.99, 33.95, 30.65, 28.97, 21.53.

MS m/z (rel int) 86 (69.2), 99 (100), 112 (16.3), 128 (39.8), 212 (2.7, M$^+$).

HRMS: found 212.1042, calcd for $C_{11}H_{16}O_4$ 212.1049.

Ref.: DiGiovanni M C et al., Tetrahedron Lett. 1993, 49, 11321.

EXAMPLE 6

Compound VIII (R'=methyl) of Scheme 3

To a solution of Compound VI from the foregoing example (50 mg, 0.24 mmol) in 2 mL methanol, 2 mL 10% NaOH was added and the solution was refluxed for 2 h. After evaporation 10 mL ether was added to the residues, its pH was adjusted to 4–5 by adding dropwise HOAc at 0° C. Methylation was conducted by adding ethereal diazomethane solution at 0° C. The solution was filtered and evaporated at 0° C. (bath). The residue was dried in vacuum (0.05 mmHg) for 2 h at 0° C. and then dissolved in $CH_2Cl_2$ (at 0° C.).

To a solution of oxalyl chloride (100 μL, 1.15 mmol) in 2 mL $CH_2Cl_2$ kept at −60° C., DMSO (180 μL, 2.54 mmol) in 1 mL $CH_2Cl_2$ was added and the mixture was stirred for 2 min. The above described solution was then added within 5 min and stirring was continued for another 15 min. Triethylamine (900 μL, 6.46 mmol) was added, the reaction mixture was stirred for 5 min and then warmed to rt. Dichloromethane (20 mL) was added and the solution was washed with 1N HCl, water and evaporated to dryness to give crude Compound VIII (R'=methyl). Purification with silica gel chromatography (hexane:EtOAc 9:1) gave pure Compound VIII (46 mg, 81%).

$^1$H NMR ($CDCl_3$) δ9.83 (s, 1H), 3.98–3.84 (m, 4H), 3.69 (s, 3H), 2.41 (dd, J=4.4, 10.9 Hz, 1H), 2.25–1.56 (m, 6H), 1.47 (s, 3H).

$^{13}$C NMR ($CDCl_3$) δ201.32, 175.92, 107.97, 64.44, 54.26, 52.15, 44.68, 33.45, 32.26, 31.97, 24.75.

MS m/z (rel int) (C,l $NH_3$) 86 (66.1), 99 (100), 127 (7.1), 155 (8.3), 211 (15.2), 243 (12.1M$^+$+1).

HRMS: found 242.1121, calcd for $Cl_{12}H_{16}O_5$ 242.1154.

Ref.: Manson A J et al., J Org Chem 1978, 43, 2480.

EXAMPLE 7

Compound IX of Scheme 3

Compound VIII (23.7 mg, 0.098 mmol) was dissolved in DCM 1.1 ml) and DBU (15 µl, 0.10 mmol) was added via syringe and the mixture was allowed to stand at room temperature for 2.5 days. 2he reaction mixture was diluted with ether (2.5 ml) and washed with 1% aqueous HCl (1 ml) and saturated aqueous $NaHCO_3$, and dried over $Na_2SO_4$. The product (17.1 mg) was a 2:1 mixture of compound VIII and compound IX.

Selected spectral data for compound IX:

$^1$H NMR ($CDCl_3$) from the mixture: δ9.63 (s, 1H), 3.74 (s, 3H) 3.23 (dd, J=12.0, 4.3 Hz, 1H) 1.25 (s, 3H). $^{13}$C NMR ($CDCl_3$) from the mixture: δ202.47, 177.02, 107.76, 64.41, 52.30, 52.05, 42.91, 33.53, 30.93, 30.57, 16.18.

GC/MS m/z (CI, $NH_3$) from the mixture: 86, 99, 243 (M+1, 100%).

The epimers were separated by HPLC on silica (eluent: hexane/MTBE, detection at 219 nm) to give pure compound IX.

$^1$H NMR ($CDCl_3$): δ9.63 (s, 1H), 3.98 (m, 4H), 3.74 (s, 3H), 3.22 (dd, J=12.0, 4.3 Hz, 1H), 1.25 (s, 3H).

MS m/z (CI, $NH_3$): 86, 99, 213, 243 (M+1, 100%), 259 (M+17).

HRMS: found 242.1120, calcd for $C_{12}H_{18}O_5$ 242.1154, found 213.1125, calcd for $C_{11}H_{17}O_4$ (M—CHO) 213.1127.

It will be appreciated that the methods of the present invention can be incorporated in the form of a variety of embodiments, only a few of which are disclosed herein. It will be apparent for the specialist that other embodiments exist and do not depart from the spirit of the invention. Thus, the described embodiments are illustrative and should not be construed as restrictive.

Scheme 1

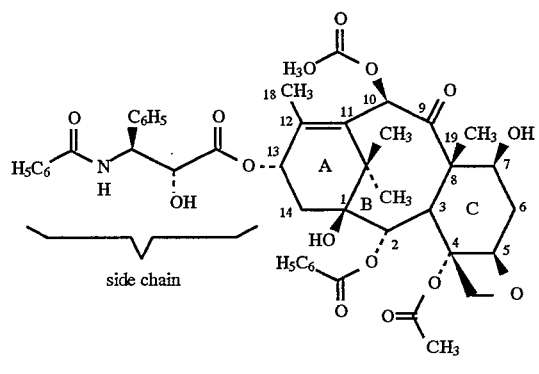

Taxol (compound 1)

Scheme 2

| Compound | $R_1$ | $R_2$ | $R_3$ |
|---|---|---|---|
| No 2 (10-deacetyl-baccatin III) | H | H | — |
| No 3 (baccatin III) | $COCH_3$ | H | — |
| No 4 (taxotere) | H | [side chain structure with $(CH_3)_3$—C—O, $C_6H_5$, OH] | — |
| No 5 | $COCH_3$ | [side chain structure with $H_5C_6$, N-H, $C_6H_5$, $OR_3$] | [structure with n=1,2] |

Scheme 2
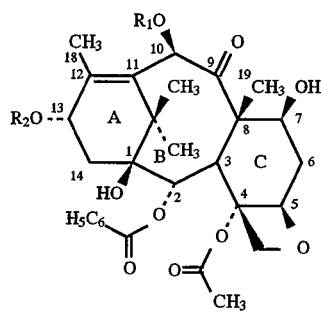
| Compound | $R_1$ | $R_2$ | $R_3$ |
|---|---|---|---|
| No 6 | $COCH_3$ | " |  |
| No 7 | $COCH_3$ | " | 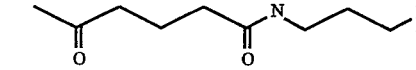 |
| No 8 | $COCH_3$ | " |  |
Scheme 3
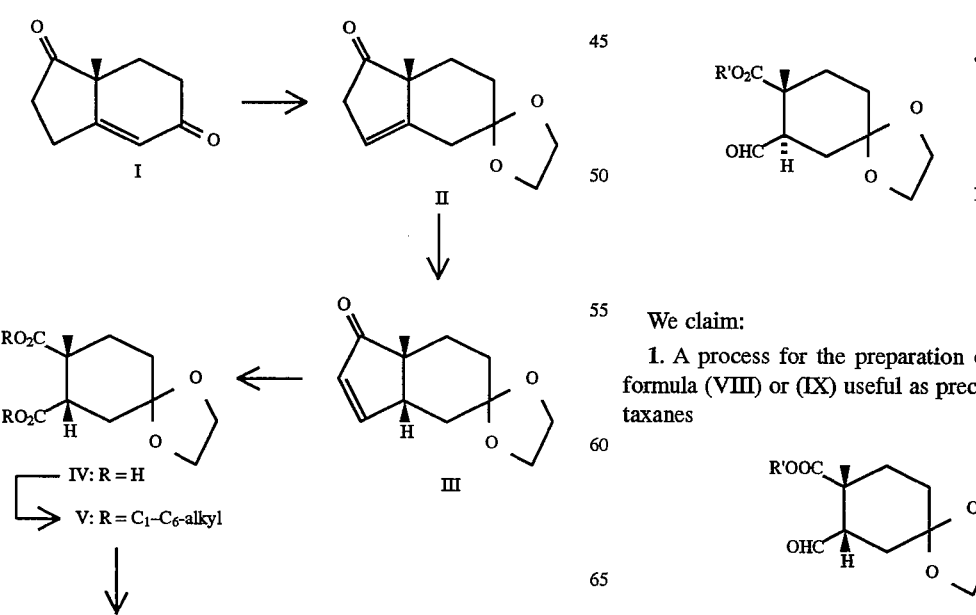
IV: R = H
V: R = $C_1$-$C_6$-alkyl
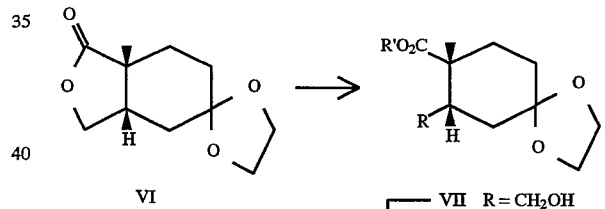
VII R = $CH_2OH$
VIII R = CHO
We claim:
1. A process for the preparation of a compound of the formula (VIII) or (IX) useful as precursor for the C-ring in taxanes
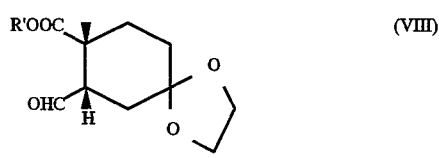
(VIII)

-continued

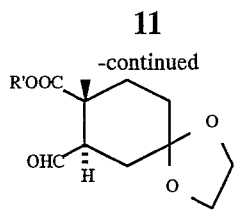 (IX)

wherein R' is a $C_1$–$C_6$-alkyl, which process comprises the steps of a) ketal protecting the carbonyl group and isomerizing the double bond in a compound of the formula (I)

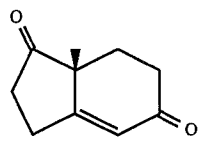 (I)

to give a compound of the formula (II)

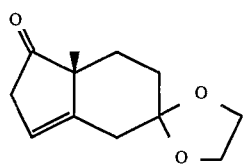 (II)

b) treating the compound of formula (II) with diazabicycloundecane in a suitable solvent to give a compound of the formula (III)

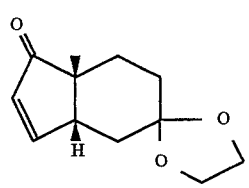 (III)

c) either i) ozonolyzing the compound (III) in methanol followed by oxidative work-up with basic hydrogen peroxide, or ii) oxidizing compound (III) with ruthenium tetraoxide of the formula $RuO_4$ generated in situ from $RuCl_3$, to give the diacid (IV)

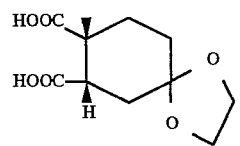 (IV)

d) either i) treating the diacid (IV) from step c) with a diazoalkane of the formula R"CHN$_2$ where "R" is hydrogen or an alkyl of 1 to 5 carbon atoms in diethylether in the presence of an acid, or ii) alkylating the diacid (IV) with a $C_1$–$C_6$-alkyl halide, to give the diester (V)

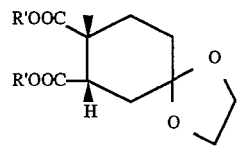 (V)

wherein $R_1$ is a $C_1$–$C_6$-alkyl, e) reducing the diester of formula (V) with diisobutylaluminumhydride in toluene to give the compound (VI)

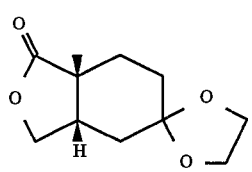 (VI)

f) opening the lactone ring of compound (VI) by treating said compound with a basic alcohol of 1 to 5 carbon atoms followed by treatment with a diazoalkane of the formula R"CHN$_2$ where R" is hydrogen or an alkyl of 1 to 5 carbon atoms to give a compound of formula (VII)

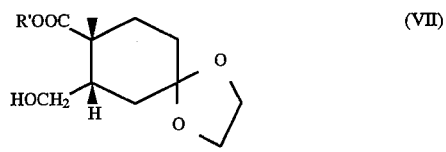 (VII)

and g) subjecting the compound (VII) to Swern oxidation in the presence of oxalyl chloride of the formula $(COCl)_2$ dimethylsulfoxide and triethylamine to give the compound of formula (VIII)

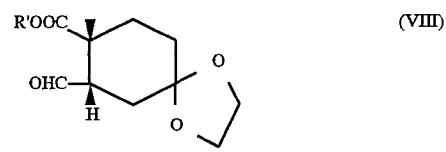 (VIII)

and optionally epimerizing compound (VIII) in the presence of diazobicycloundecane to give a mixture of compound (VIII) and compound (IX)

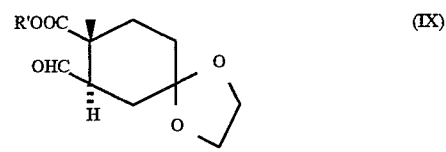 (IX)

which further is separated into the compound (VIII) and (IX).

2. The process according to claim 1 wherein the diazoalkane is diazomethane.

3. A compound having the formula (VIII) or (IX)

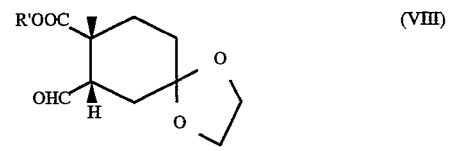 (VIII)

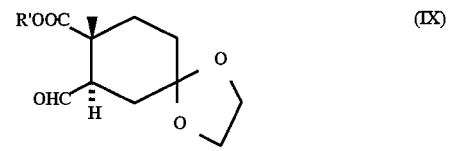 (IX)

wherein R' is a $C_1$–$C_6$ alkyl group.

4. A compound according to claim 3 wherein R' is methyl.

5. A compound having the formula (III)

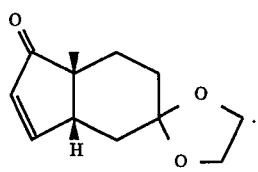

6. A compound having the formula (IV)

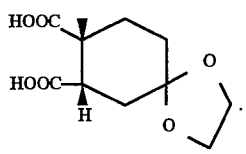

7. A compound having the formula (V)

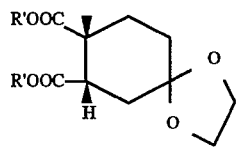

wherein R' is a $C_1$–$C_6$ alkyl group.

8. A compound according to claim 7 wherein R' is methyl.

9. A compound having the formula (VI)

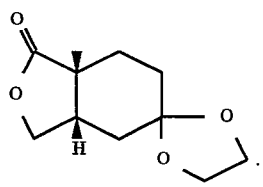

10. A compound having the formula (VII)

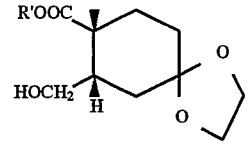

wherein R' is a $C_1$–$C_6$ alkyl group.

11. A compound according to claim 10 wherein R' is methyl.

12. The process according to claim 1 wherein the solvent in step b) is a lower alcohol of 1 to 5 carbon atoms or is acetonitrile.

13. The process according to claim 1 wherein the ruthenium tetraoxide in step c) is generated in situ from $RuCl_3$ with sodium periodate.

14. The process according to claim 1 wherein the separation in step g) is by HPLC.

* * * * *